United States Patent [19]

Shibuya et al.

[11] Patent Number: 5,236,496
[45] Date of Patent: Aug. 17, 1993

[54] PASTE COMPOSITION AND METHOD FOR PREPARING THE SAME

[75] Inventors: Mutsumi Shibuya; Satomi Ishii, both of Tokyo, Japan

[73] Assignee: Showa Yakuhin Kako Co., Ltd., Tokyo, Japan

[21] Appl. No.: 714,619

[22] Filed: Jun. 13, 1991

[30] Foreign Application Priority Data

Jun. 26, 1990 [JP] Japan .................. 2-167788

[51] Int. Cl.$^5$ .................. C08L 1/32; C08L 1/10; A61B 12/00; A61K 33/00
[52] U.S. Cl. .................. 106/189; 106/198; 106/35; 106/203; 106/795; 106/805; 424/49; 424/692; 424/693; 424/722; 128/898; 433/228.1
[58] Field of Search .................. 106/189, 198, 35, 203, 106/795, 805; 424/49, 692, 693, 722; 128/898; 433/228.1

[56] References Cited

U.S. PATENT DOCUMENTS

| | | | |
|---|---|---|---|
| 2,065,664 | 12/1936 | Dickie et al. .................. | 106/189 |
| 2,599,445 | 6/1952 | Gordon .................. | 106/795 |
| 3,047,408 | 7/1962 | Dougherty .................. | 106/795 |
| 3,285,756 | 11/1966 | Morén .................. | 106/795 |
| 4,315,779 | 2/1982 | Heyd et al. .................. | 106/189 |

OTHER PUBLICATIONS

Chemical Abstracts, 782w, vol. 77, No. 1, Jul. 3, 1972, U. Schroder, et al., "Early Reaction of Intact Human Teeth to Calcium Hydroxide Following Experimental Pulpotomy and Its Significance for the Development of Hard Tissue Barrier".

*Primary Examiner*—David Brunsman
*Attorney, Agent, or Firm*—Oblon, Spivak, McClelland, Maier & Neustadt

[57] ABSTRACT

Paste compositions comprising from 20 to 60% by weight of an alkaline-earth metal hydroxide selected from the group consisting of calcium hydroxide, magnesium hydroxide, strontium hydroxide, and the mixture threreof; from 20 to 60% by weight of a polyhydric alcohol; from 0.5 to 5% by weight of an alkali-soluble cellulose derivative; and from 5 to 20% by weight of water based on the total weight of the composition are disclosed. Also disclosed are a method for preparing the same; a medicament useful for pulpotomy, medicament for stimulating the formation of osteoid scar; and a method for pulpotomy and a method for osteosis comprising the step of applying the above composition.

12 Claims, No Drawings

PASTE COMPOSITION AND METHOD FOR PREPARING THE SAME

BACKGROUND OF THE INVENTION

1. Field of the Invention

The present invention relates to a paste composition comprising an alkaline earth metal hydroxide. More specifically, the present invention relates to a paste composition useful as a medicament, which stimulates the formation of osteoid scar. The present invention also relates to a method for preparing the paste composition comprising an alkaline earth metal hydroxide.

2. Description of the Related Art

Alkaline-earth metal hydroxides have been known to have biological activities such as, for example, stimulation of the formation of osteoid scar.

For example, in dentistry, calcium hydroxide can be used as a medicament in treatments for conservating teeth such as, for example, root canal fillings or vital amputation of the pulp.

The method of root canal filing comprises the steps of extirpating the pulp of a diseased tooth, and compactly filling with a filling material in order to conserve the tooth. CALBITAL (Neo Seiyaku Kogyo, Japan) is one example of an available filling material comprising calcium hydroxide. However, the above filling material has been found to be inconvenient since dentists are required to mix, in situ, a powdery component and a liquid component to obtain a paste composition suitable for dental application.

Vital amputation of the pulp is a method for conserving teeth together with a partially conserved healthy dental pulp. An example of the method is a pulpotomy using calcium hydroxide. The pulpotomy comprising the use of calcium hydroxide includes the steps of (1) mechanically amputating the diseased part of dental pulp, and (2) applying on the section of the pulp a paste composition which is prepared, in situ, by kneading powdery calcium hydroxide with sterile water in order to have the surface of the sectioned pulp form osteoid scar, i.e., dentin bridge. According to this method, however, it is necessary for a dentist to knead powdery calcium hydroxide and sterile water, in situ, under sterile conditions using previously sterilized dental instruments such as a kneading plate and spatula.

VITAPEX, a prepared one component paste composition which comprises calcium hydroxide and a silicon oil base material, is available from Neo Seiyaku Kogyo, Japan. However, this composition is not likely to induce the formation of osteoid scar since calcium hydroxide remains uneluted in the oil-based composition.

Further, a past composition obtained by kneading calcium hydroxide and water is unstable since powdery calcium hydroxide stearates or the composition sets after being dried. A gel forming material such as, for example, a water-soluble polymer added to an aqueous component does not help stabilize and thicken the paste composition.

SUMMARY OF THE INVENTION

An object of the present invention is to provide a hydrophilic paste composition comprising an alkaline-earth metal hydroxide which extensively eliminates undesired problems mentioned above.

Another object of the present invention is to provide a method for preparing the paste composition.

Further objects of the present invention are to provide a medicament useful for pulpotomy and to provide a medicament stimulating the formation of osteoid scar.

Yet another object of the present invention is to provide a method of pulpotomy which comprises the step of applying said composition to a section of pulp.

The inventors of the present invention have conducted various studies to achieve the foregoing objects and found that the objects can be effectively attained by providing a paste composition prepared by a process comprising the step of kneading a hydroxide selected from the group consisting of calcium hydroxide, magnesium hydroxide, strontium hydroxide, and the mixture thereof, with a base material comprising water, an alkali-soluble cellulose derivative, and a polyhydric alcohol. The inventors have also found that this uniform pasty composition has excellent stimulation of the formation of osteoid scar and is stable if stored for a long time.

Thus, in accordance with the above objects, the present invention provides a pasty composition which comprises from 20 to 60% by weight of an alkaline-earth metal hydroxide selected from the group consisting of calcium hydroxide, magnesium hydroxide, strontium hydroxide, and the mixture threreof; from 20 to 60% by weight of polyhydric alcohol; from 0.5 to 5% by weight of an alkali-soluble cellulose derivative; and from 5 to 20% by weight of water based on the total weight of the composition.

In accordance with another embodiment of the present invention, there is provided a process for preparing said paste composition, which comprises the steps of dispersing from 0.5 to 5% by weight of an alkali-soluble cellulose derivative in 5 to 20% by weight of water; adding from 20 to 60% by weight of polyhydric alcohol to the dispersion obtained above; adding from 20 to 60% by weight of an alkaline-earth metal hydroxide to the mixture obtained above; and kneading the mixture to obtain a uniform paste composition.

In accordance with yet another embodiment, the present invention provides a medicament useful for pulpotomy.

In accordance with a still further embodiment, the present invention provides a medicament for stimulating the formation of osteoid scar.

The invention also provides a method of pulpotomy which comprises the step of applying said composition to a section of pulp, and a method for osteosis which comprises the step of applying said composition in order to stimulate the formation of osseous tissue.

Further objects, features and advantages of the present invention will become apparent from the Description of the Preferred Embodiments which follows, when read in light of the attached Examples.

DETAILED DESCRIPTION OF THE PREFERRED EMBODIMENTS

The alkaline-earth metal hydroxides used in the present invention are selected from the group consisting of calcium hydroxide, magnesium hydroxide, strontium hydroxide, and the mixture threreof. Commercially available alkaline earth metal hydroxides, which are generally prepared in the form of powder, may preferably be used. For example, alkaline-earth metal hydroxides having a particle size of from 30 to 50 $\mu m$, which are valuated according to the Japanese Industrial Standard (JIS), may be used.

The polyhydric alcohols used in the present invention are defined to be alcohols having not less than two hydroxyl groups in the molecule. Examples of the polyhydric alcohol include glycols such as, for example, propylene glycol; polyalkylene glycols such as, for example, polyethylene glycol and polypropylene glycol; glycerol; and mixtures thereof. Preferably, propylene glycol may be used. Where polymeric polyhydric alcohols are used, polyethylene glycol having an average molecular weight of about 400 and polypropylene having an average molecular weight of about 1,000 may preferably be used.

The alkali-soluble cellulose derivatives used in the present invention are defined to be cellulose derivatives soluble in alkaline solutions. Examples of the alkali-soluble cellulose derivatives include, for example, hydroxypropylmethylcellulose acetate succinate, hydroxypropylmethylcellulose phthalate, cellulose acetate phthalate, and the mixtures thereof. Preferably, hydroxypropylmethylcelulllose acetate succintate may be used. Hydroxypropylmethylcellulose acetate succinate having an average molecular weight of about $8.0 \times 10^4$, hydroxymethylcellulose phthalate having the average molecular weight of about $8.4 \times 10^4$, and cellulose acetate phthalate having an average molecular weight of about $8.2 \times 10^4$ are preferably used. The preferably used alkali-soluble cellulose derivatives are those soluble in 0.1N aqueous sodium hydroxide solution at a concentration of not less than 2% by weight.

Water used in the present invention may be distilled water, ion-exchanged water, or distilled water for injection. Preferably, distilled water is be used.

The paste composition of the present invention comprises the above-mentioned components in a ratio of from 20 to 60% by weight of an alkaline-earth metal hydroxide selected from the group consisting of calcium hydroxide, magnesium hydroxide, strontium hydroxide, and the mixtures thereof; from 20 to 60% by weight of a polyhydric alcohol; from 0.5 to 5% by weight of an alkali soluble cellulose derivative; and from 5 to 20% by weight of water, all of the above percentages being based on the total weight of the composition.

If the polyhydric alcohol content of the paste composition is too low, it will become impossible for the paste composition to retain water and, as a result, a smooth paste composition cannot be obtained. If the polyhydric alcohol content is too high, the viscosity of the composition will become too low, which results in the separation of the polyhydric alcohol from the paste composition. If the alkali-soluble cellulose content of the paste composition is too low, the thixotropic property Of the composition will be decreased and, as the result, water will become separated from the paste composition. If the alkali-soluble cellulose content is too high, the paste composition will become too hard to have appropriate fluidity. Further, if the water content of the paste composition is too low, the alkali-soluble cellulose cannot be fully disolved in the composition, with the result that the composition obtained is not sufficiently pasty. If the water content of the paste composition is too high, the composition obtained will be prone to lack of smoothness, which results in the separation and appearance of water on the surface of the composition. Preferably, the paste composition of the present invention comprises from 40 to 50% by weight of the alkaline-earth metal hydroxide selected from the group consisting of calcium hydroxide, magnesium hydroxide, strontium hydroxide, and the mixture threreof; from 20 to 30% by weight of the polyhydric alcohol; from 1 to 2% by weight of the alkali-soluble cellulose derivative; and from 10 to 15% by weight of water based on the total weight of the composition.

The paste composition of the present invention is prepared in the form of a paste which has a viscosity of not less than 100 P, and comprises finely divided particles having an average particle size of not more than 10 $\mu$m. The paste composition of the present invention is a basic composition having a pH of from 11 to 13.

According to the present invention, there is provided a method for preparing the paste composition described above, which comprises the steps of dispersing from 0.5 to 5 % by weight of an alkali-soluble cellulose derivative in water in an amount of from 5 to 20% by weight; adding from 20 to 60% by weight of polyhydric alcohol to the dispersion obtained above; adding from 20 to 60% by weight of an alkaline-earth metal hydroxide selected from the group consisting of calcium hydroxide, magnesium hydroxide, strontium hydroxide, and the mixture threreof to the mixture obtained above; and kneading the mixture to obtain a uniform paste composition.

A preferred embodiment of the method for preparing the paste composition of the present invention comprises the steps of dispersing 1 part by weight of hydroxypropylmethylcellulose acetate succinate in 10 parts by weight of water; adding 30 parts by weight of propylene glycol to the dispersion obtained above; adding 45 parts by weight of finely powdered calcium hydroxide (mesh 325) to the mixture obtained; and kneading the mixture to obtain a uniform pasty composition.

The method for preparing the paste composition of the present invention described above may comprise the step of adding additives to the paste composition. Examples of the additive include, for example, contrast mediums such as, for example, barium sulfate or bismuth subcarbonate; and antibacterial agents such as, for example, benzethonium chloride or benzalkonium chloride. In general, the paste composition of the present invention may include, for example, from 10 to 20 parts by weight of contrast medium and from 1 to 2 parts by weight of antibactrial agent. The paste composition of the present invention may generally be prepared under aseptic manipulation. In addition, the paste composition manufactured or the composition divided and filled in containers may optionally be sterilized under appropriate sterile conditions.

The paste compositions of the present invention, preferably the paste compositions comprising calcium hydroxide, stimulate the formation of osteoid scar and are useful as a medicament for pulpotomy. The paste compositions of the present invention have excellent adhesion to dental pulp and tooth substance when applied to a section of pulp or the wall of a pulp canal, and as a consequence, the paste composition can remain on the applied location for a long time so as to effectively stimulate the formation of osseous tissue. In general, the unit dose of the paste composition of the present invention may be, for example, from 5 to 20 mg for a pulpotomy. A pulpotomy comprises the step of applying an appropriate amount of said composition to the surface of the sectioned pulp in the same manner as the application of an ointment to a diseased part. The paste composition of the present invention is also useful for osteosis and may be used in surgery. The method for osteosis comprises the step of applying said composition, which is coated on cloth or a plastic film in the same manner as a cataplasm, to a diseased part in the amount of, for example, from 40 to 50 mg.

The present invention will be further illustrated by the following Examples. The Examples are given by way of illustration only and are not to be construed as limiting.

EXAMPLE 1

The prepared composition had the following components:

| | |
|---|---|
| Calcium hydroxide | 500 g (50% by weight) |
| Propylene glycol | 350 g (35% by weight) |
| Hydropropylmethylcellulose acetate succinate | 15 g (1.5% by weight) |
| Distilled water | 135 g (13.5% by weight) |

Hydroxypropylmethylcellulose acetate succinate, propylene glycol, and calcium hydroxide were added to water in the described order, and the mixture obtained was kneaded to form a uniform paste composition, which was then filled in a dental syringe. The viscosity, the average particle size, and the pH of the composition obtained were 550 P at 20° C., 30 μm, and 12.7, respectively.

EXAMPLE 2

The prepared composition had the following components:

| | |
|---|---|
| Calcium hydroxide | 45% by weight |
| Propylene glycol | 45% by weight |
| Hydroxypropylmethylcellulose phthalate | 0.5% by weight |
| Distilled water | 9.5% by weight |

The paste composition of the present invention was prepared in the same manner as described in Example 1. The viscocity, the average particle size, and the pH of the composition obtained were 400 P at 20° C., 30 μm, and 12.0, respectively.

EXAMPLE 3

The prepared composition had the following components:

| | |
|---|---|
| Calcium hydroxide | 55% by weight |
| Polyethylene glycol | 35% by weight |
| Cellulose acetate phthalate | 1.0% by weight |
| Distilled water | 9.0% by weight |

The paste composition of the present invention was prepared in the same manner as described in Example 1. The viscocity, the average particle size, and the pH of the composition obtained were 270 P at 20° C., 30 μm, and 11.9, respectively.

EXAMPLE 4

The prepared composition had the following components:

| | |
|---|---|
| Calcium hydroxide | 42% by weight |
| Glycerol | 38% by weight |
| Hydroxypropylmethylcellulose phthalate | 2.0% by weight |
| Distilled water | 18% by weight |

The paste composition of the present invention was prepared in the same manner as described in Example 1. The viscocity, the average particle size, and the pH of the composition obtained were 450 P at 20° C., 30 μm, and 11.0, respectively.

EXAMPLE 5

The prepared composition had the following components:

| | |
|---|---|
| Calcium hydroxide | 55% by weight |
| Glycerol | 27% by weight |
| Cellulose acetate phthalate | 1.0% by weight |
| Distilled water | 17% by weight |

The paste composition of the present invention was prepared in the same manner as described in Example 1. The viscocity, the average particle size, and the pH of the composition obtained were 400 P at 20° C., 30 μm, and 12.3, respectively.

EXAMPLE 6

After being stored for three months at a temperature of from 20 to 26° C. (the average temperature of 22.5° C.) under a humidity of from 45 to 80% RH (the average humidity of 65% RH), the stabilities of the paste compositions prepared according to Examples 1 to 5 were determined by measuring the viscosities of the composition and by observing the separation of the components of the paste composition. The viscosity of the composition was measured by a rotational viscometer set in a thermostat. In order to observe the separation of the components of the composition, about 2 ml of the pasty composition was filled in a transparent syringe of 6.7 mm inside diameter and 55 mm length, and the syringe was kept in a light-resistant paper box. From the results summarized in the following Table 1, it will be clearly understood by those of ordinary skill in the art that the paste composition of the present invention is stable if stored under ambient conditions for a long time.

TABLE 1

| | Example No. | | | | |
|---|---|---|---|---|---|
| | 1 | 2 | 3 | 4 | 5 |
| Viscosity (P) | 550 | 400 | 450 | 400 | 400 |
| Separation | —* | — | — | — | — |

*(—): The separation of the components was not observed.

One of ordinary skill in the art will recognize that improvements and modifications may be made while remaining within the scope of the present invention. The scope of the present invention is determined soley by the appended claims.

What is claimed is:

1. A paste composition which comprises from 20 to 60% by weight of an alkaline-earth metal hydroxide selected from the group consisting of calcium hydroxide, magnesium hydroxide, strontium hydroxide, and mixtures thereof; from 20 to 60% by weight of a polyhydric alcohol; from 0.5 to 5% by weight of an alkali-soluble cellulose derivative; and from 5 to 20% by weight of water, all of the above percentages being based on the total weight of the composition.

2. The paste composition according to claim 1, wherein the alkaline-earth metal hydroxide is calcium hydroxide.

3. The paste composition according to claim 1, wherein the polyhydric alcohol is propylene glycol.

4. The paste composition according to claim 1, wherein the polyhydric alcohol is polyethylene glycol having a molecular weight of about 400.

5. The paste composition according to claim 1, wherein the polyhydric alcohol is polypropylene glycol having an average molecular weight of about 1,000.

6. The paste composition according to claim 1, wherein the paste composition comprises from 40 to 50% by weight of the alkaline-earth metal hydroxide; from 20 to 30% by weight of the polyhydric alcohol; from 1 to 2% by weight of the alkali-soluble cellulose derivative; and from 10 to 15% by weight of water, all percentages being based on the total weight of the composition.

7. A paste composition which comprises from 20 to 60% by weight of an alkaline-earth metal hydroxide selected form the group consisting of calcium hydroxide, magnesium hydroxide, strontium hydroxide, and mixtures thereof; from 20 to 60 % by weight of a polyhudric alcohol; from 0.5 to 5% by weight of an alkali-soluble cellulose derivative; and from 5 to 20% by weight of water, all of the above percentages being based on the total weight of the composition, wherein the alkali-soluble cellulose derivative is hydroxypropylmethylcellulose acetate succinate having a molecular weight of about $8.0 \times 10^4$.

8. A paste composition which comprises from 20 to 60% by weight of an alkaline-earth metal hydroxide selected form the group consisting of calcium hydroxide, magnesium hydroxide, strontium hydroxide, and mixtures thereof; from 20 to 60% by weight of a polyhydric alcohol; from 0.5 to 5% by weight of an alkali-soluble cellulose derivative; and from 5 to 20% by weight of water, all of the above percentages being based on the total weight of the composition, wherein the alkali-soluble cellulose derivative is hydroxymethylcelullose phthalate having an average molecular weight of about $8.4 \times 10^4$.

9. A paste composition which comprises from 20 to 60% by weight of an alkaline-earth metal hydroxide selected form the group consisting of calcium hydroxide, magnesium hydroxide, strontium hydroxide, and mixtures thereof; from 20 to 60% by weight of a polyhydric alcohol; from 0.5 to 5% by weight of an alkali-soluble cellulose derivative; and from 5 to 20% by weight of water, all of the above percentages being based on the total weight of the composition, wherein the alkali-soluble cellulose derivative is celullose acetate phthalate having an average molecular weight of about $8.2 \times 10^4$.

10. A process for preparing a paste composition comprising from 20 to 60% by weight of an alkaline-earth metal hydroxide selected from the group consisting of calcium hydroxide, magnesium hydroxide, strontium hydroxide, and the mixture thereof; from 20 to 60% by weight of a polyhydric alcohol; from 0.5 to 5% by weight of an alkali-soluble cellulose derivative; and from 5 to 20% by weight of water, all percentages based on the total weight of the composition, which process comprises the steps of:

dispersing from 0.5 to 5% by weight of an alkali-soluble cellulose derivative in water in an amount of from 5 to 20% by weight;

adding from 20 to 60% by weight of polyhydric alcohol to the dispersion obtained above;

adding from 20 to 60% by weight of an alkaline-earth metal hydroxide selected from the group consisting of calcium hydroxide, magnesium hydroxide, strontium hydroxide, and the mixture threreof to the mixture obtained above; and kneading the mixture to obtain a uniform paste composition.

11. A pulpotomy method which comprises the step of applying to the surface of the sectioned pulp a paste composition comprising from 20 to 60% by weight of an alkaline-earth metal hydroxide selected from the group consisting of calcium hydroxide, magnesium hydroxide, strontium hydroxide, and the mixture threreof; from 20 to 60% by weight of a polyhydric alcohol; from 0.5 to 5% by weight of an alkali-soluble cellulose derivative; and from 5 to 20% by weight of water based on the total weight of the composition, wherein the composition is applied in an amount sufficient to form dentin bridge on the sectioned pulp.

12. A osteosis method which comprises the step of applying to diseased part of a patient a paste composition comprising from 20 to 60% by weight of an alkaline-earth metal hydroxide selected from the group consisting of calcium hydroxide, magnesium hydroxide, strontium hydroxide, and the mixture threreof; from 20 to 60% by weight of a polyhydric alcohol; from 0.5 to 5% by weight of an alkali-soluble cellulose derivative; and from 5 to 20% by weight of water based on the total weight of the composition, wherein the composition is applied in an amount suffceint to stimulate the formation of osseous tissue.

* * * * *